(12) United States Patent
Couturier et al.

(10) Patent No.: US 6,700,007 B2
(45) Date of Patent: Mar. 2, 2004

(54) METHOD FOR PREPARING ALKOXYAMINES FROM NITROXIDES

(75) Inventors: Jean-Luc Couturier, Lyons (FR); Olivier Guerret, Marcy l'Etoile (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/089,720

(22) PCT Filed: Aug. 2, 2001

(86) PCT No.: PCT/FR01/02526

§ 371 (c)(1),
(2), (4) Date: Aug. 8, 2002

(87) PCT Pub. No.: WO02/12149

PCT Pub. Date: Feb. 14, 2002

(65) Prior Publication Data

US 2003/0050507 A1 Mar. 13, 2003

(30) Foreign Application Priority Data

Aug. 4, 2000  (FR) ............................................. 00 10344

(51) Int. Cl.[7] ........................... C07C 239/20; C07F 9/40
(52) U.S. Cl. ........................ 558/145; 558/175; 564/300; 564/301
(58) Field of Search ................................. 558/145, 175; 564/300, 301

(56) References Cited

U.S. PATENT DOCUMENTS 3,046,308 A  *  7/1962  Dunn et al. .................. 260/584
3,163,677 A  * 12/1964  Hoffman et al. ............. 260/583
6,495,720 B1 * 12/2002  Couturier et al. ........... 564/301

FOREIGN PATENT DOCUMENTS

WO            98 40415        9/1998

* cited by examiner

*Primary Examiner*—Brian Davis
(74) *Attorney, Agent, or Firm*—Millen, White, Zelano & Branigan, P.C.

(57) ABSTRACT

A process for preparing alkoxyamines in a biphasic medium comprises mixing an ionic liquid, an organic solvent, a metal salt, a ligand for the metal, a halocarbon compound ZX and a nitroxide, keeping the reaction medium stirring at a temperature of between 20° C. and 90° C. until the nitroxide has disappeared, separating the mixture by decantation, recovering the organic phase, and optionally washing it with water and then isolating the alkoxyamine by evaporating the organic solvent under reduced pressure.

21 Claims, No Drawings

METHOD FOR PREPARING ALKOXYAMINES FROM NITROXIDES

The present invention relates to a process for preparing α,β,β-trisubstituted hydroxylamines, referred to hereinbelow as alkoxyamines, obtained from nitroxides, which can be used in particular as radical-polymerization initiators. The use of alkoxyamines such as those derived from (2,2,6,6-tetramethylpiperidyl)-N-oxide (TEMPO) in the preparation of macromolecules has given rise to many publications.

Thus, Hawker C. J. et al. (Macromolecules 1996, 29, pages 5245–5254) showed that the use of TEMPO-based alkoxyamines such as (2',2',6',6'-tetra-methyl-1'-piperidyloxy)methylbenzene as initiators for the radical-mediated polymerization of styrene made it possible to control the polymerization and to gain access to well-defined polymers with low polydispersity indices, and they found that the polymerization rates were substantially equivalent to the rates obtained when they used conventional initiators such as AIBN or benzoyl peroxide in the presence of TEMPO.

Alkoxyamines can be prepared according to methods known in the literature. The most common method involves the coupling of a carbon radical with a nitroxide radical.

If an alkoxyamine is denoted by:

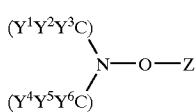
(I)

$Y^1$, $Y^2$, $Y^3$, $Y^4$, $Y^5$, $Y^6$, Z being defined later, the carbon radical Z˙ can be generated by various methods described in the literature: decomposition of an azo compound, abstraction of a hydrogen atom from a suitable substrate, addition of a radical to an olefin. The radical Z˙ can also be generated from an organometallic compound such as an organomagnesium reagent Z-MgX as described by Hawker C. J. et al. in Macromolecules 1996, 29, 5245–5254 or from a halo derivative Z-X in the presence of an organometallic system such as CuX/bipyridine (X=Cl or Br) according to a reaction of ATRA (Atom Transfer Radical Addition) type as described by Dorota Greszta et al. in Macromolecules 1996, 29, 7661–7670.

One of the methods most commonly used for preparing alkoxyamines (I) is the method involving the ATRA reaction.

This method consists in transferring an atom or a group of atoms onto another molecule in the presence of a CuX/bipyridine organometallic system, in solvent medium, according to the scheme:

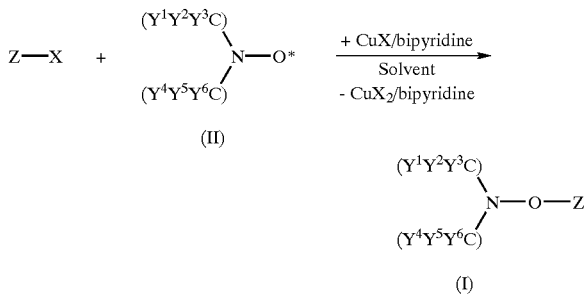

In the organometallic system, X preferably represents a bromine, chlorine or iodine atom.

The procedure generally used consists in dissolving the organometallic system such as CuBr/bipyridine in an organic solvent, preferably an aromatic solvent such as benzene or toluene, and then in introducing the compound ZX and the nitroxide (II) into the solution.

This approach has the major drawback of requiring long reaction times, that are unacceptable for an industrial preparation of alkoxyamines, or of using a large excess of one of the reagents.

In addition, the removal of the residual metal from the products obtained is difficult, requiring expensive purification operations such as passing the products through a column of silica.

Thus, in international patent application WO 98/40415, for example, Matyjaszewski K. et al. obtain 1-(2,2,6,6-tetramethylpiperidyloxy)-1-phenylethane in a yield of 69% after purification by column chromatography, by reacting TEMPO and (1-bromoethyl)benzene in a TEMPO/(1-bromoethyl)benzene molar ratio of 2 (i.e. a molar excess of TEMPO equal to 100%) for 2 hours at 90° C., in the presence of an organometallic system [4,4'-bis(5-nonyl)-2,2'-bipyridine/Cu(OTf)$_2$/Cu$^0$].

A process has now been found for preparing alkoxyamines of formula:

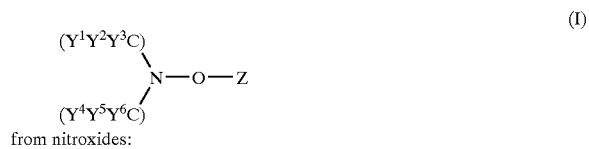
(I)

from nitroxides:

(II)

the said process consisting in reacting the said nitroxide (II) with a halocarbon compound ZX in which X represents a chlorine, bromine or iodine atom, in the presence of an organometallic system MA$_n$(L)$_y$ (III) in which:

M represents a transition metal with an oxidation state n such that it can participate in a redox reaction with the transferable atom or group, A represents a halogen atom, a carboxylate group or a triflate group, L represents a ligand for the metal M, y is equal to 1, 2 or 3, n is equal to 1, or 2, according to the scheme:

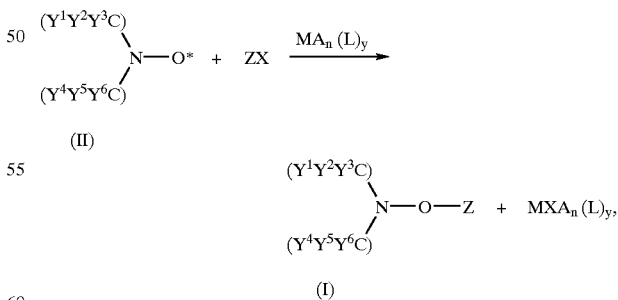

the said process being characterized in that the procedure is carried out in a biphasic medium comprising at least one ionic liquid and an organic solvent which is immiscible with the said ionic liquid.

The process according to the invention consists in carrying out the following steps:

a) a metal salt $MA_n$, optionally a metal X with an oxidation state zero, a ligand L, at least one ionic liquid, an organic solvent, the halo carbon compound ZX and the nitroxide (II) are mixed, with stirring, in a ZX/nitroxide (II) molar ratio ranging from 1 to 1.5, and preferably close to 1;

b) the reaction medium is kept stirring at a temperature of between 20° C. and 90° C., and preferably at a temperature ranging from 20° C. to 35° C., until the nitroxide (II) has completely disappeared; and then c) the stirring is stopped, the mixture is separated by decantation, the organic phase is recovered and optionally washed with water, and then d) the alkoxyamine (I) is isolated from the organic phase by evaporating the organic solvent under reduced pressure, and e) optionally, the ionic liquid phase is recycled at least once with regeneration of the active species of the metal $M(M^n)$.

According to the present invention, the number of recyclings of the ionic liquid phase is not limiting. Preferably, the ionic liquid phase will be recycled a number of times ranging from 1 to 10.

According to the present invention, the expression ionic liquids refers to organic salts which are liquid at reaction temperatures.

By way of illustration of organic salts which can be used according to the present invention, mention will be made of ammonium, pyridinium, imidazolium, triazolium, guanidinium, phosphonium or sulphonium salts. The anion may be, inter alia, a halide such as $Cl^-$, $Br^-$, $I^-$, a tin halide such as $SnCl_3^-$, a germanium halide such as $GeCl_3^-$, a gallium halide such as $GaCl_3^-$, an aluminium halide such as $AlCl_4^-$, $Al_2Cl_7^-$, $Al_3Cl_{10}^-$, a transition metal halide such as $CuCl_2^-$, a boron, antimony or phosphorus fluoride such as $BF_4^-$, $SbF_6^-$ or $PF_6^-$, a carboxylate such as $CF_3CO_2^-$, a sulphonate such as $CF_3SO_3^-$ or $FSO_3^-$, an amide such as $(CF_3SO_2)_2N^-$, a tetralkyl or tetraaryl boride such as $B(C_6F_5)_4^-$. The cation and the anion of the salt or of the mixture of salts will be appropriately chosen in order to have a liquid at the reaction temperature. Optionally, the ionic liquid may contain water. According to the present invention, use will be preferably made of N,N'-dialkylimidazolium salts. By way of example of such salts, mention will be made of:

1-butyl-3-methylimidazolium chloride,
1-propyl-3-methylimidazolium chloride,
1propyl-3-methylimidazolium bromide.

The organic solvent is chosen so as to have a biphasic system with the ionic liquid(s). Preferably, the organic solvent will be chosen from aliphatic or aromatic hydrocarbons, or alternatively from ethers. Toluene will be most particularly used.

According to the present invention, M preferably represents Cu(I), Fe(II), Ni(II), and most particularly Cu(I).

The active species of the metal M, hereinbelow $M^n$, is generated from a metal salt, preferably a metal halide $M^n X_n$. It may also be generated in situ according to a redox reaction of the type:

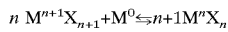

in which the $^M$ of the metal M represents the oxidation state of the said metal, $M^0$ represents the metal M with the oxidation state zero and n=1 or 2.

Overall, the $M^n/RX$ ratio should be at least equal to 1. The preferred metal halide is CuBr.

Preferably, A represents a halogen such as Cl or Br, a carboxylate group such as acetate or a triflate group and X represents a chlorine atom or a bromine atom.

According to the present invention, the ligand L which co-ordinates with the metal M may contain one or more nitrogen, phosphorus, oxygen or sulphur atoms. The preferred ligands are the linear polyamines represented by the general formula (IV):

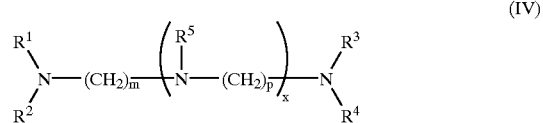

in which $R^1$, $R^2$, $R^3$ and $R^4$, which may be identical or different, represent a hydrogen atom, a linear or branched alkyl group containing a number of carbon atoms ranging from 1 to 10 and preferably ranging from 1 to 4, $R^5$ represents a hydrogen atom, a linear or branched alkyl group containing a number of carbon atoms ranging from 1 to 10 and preferably ranging from 1 to 4, a residue

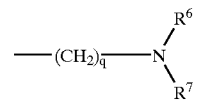

in which $R^6$ and $R^7$ have the same meanings as $R^5$, or alternatively at least two of the radicals $R^1$, $R^2$, $R^3$, $R^4$ and $R^5$ may be linked together to form a ring; m, p and q, which may be identical or different, represent integers ranging from 1 to 4, preferably equal to 2, x ranging from 0 to 4.

By way of illustration of ligands L represented by formula (IV) mention will be made of:

tris[2-(dimethylamino)ethyl]amine:

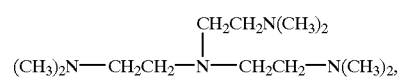

N,N,N',N',N"-pentamethyldiethylenetriamine (PMDETA):

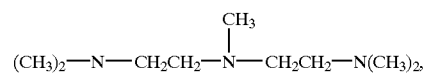

N,N,N',N'-tetramethylethylenediamine:
$(CH_3)_2$—N—$CH_2CH_2$—N—$(CH_3)_2$, 1,1,4,7,10,10-hexamethyltriethylenetetramine (HMTETA):

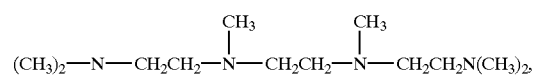

N,N-dimethyldipropylenetriamine (DMAPAPA):

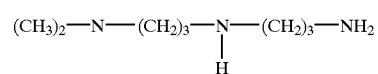

cyclic polyamines such as:
1,4,7-trimethyl-1,4,7-triazacyclononane,
1,5,9-trimethyl-1,5,9-triazacyclododecane,
1,4,8,11-tetramethyl-1,4,8,11-tetraazacyclotetradecane.
PMDETA and DMAPAPA will preferably be used.

The ligand L as defined above is used in an L/M$^n$ (molar) ratio ranging from 0.2 to 4, and preferably ranging from 0.4 to 2.

The process according to the invention therefore consists in mixing, with vigorous stirring, at least one ionic liquid with a metal salt, a ligand L, the compound with transferable atoms or groups RX, the nitroxide II and optionally the metal M with the oxidation state zero and an organic solvent.

The reaction is carried out at a temperature of between 20° C. and 90° C., preferably in the region of room temperature. The process is performed under an atmosphere of inert gas such as nitrogen or argon and preferably at atmospheric pressure.

The end of the reaction can be monitored by the disappearance of the reagents by chromatographic methods (GC, HPLC, TLC). Once the reaction is complete, the reaction mixture is separated-by decantation. The organic phase is recovered. The ionic liquid phase may be optionally extracted with the reaction organic solvent. The alkoxyamines (I) are recovered by conventional treatments of the organic phase such as washes with water followed by evaporation of the solvent. The alkoxyamines (I) may be characterized by elemental analysis HPLC, IR and NMR.

According to the present invention, the ionic liquid phase may be reused for another ATRA reaction. The regeneration of the organometallic system may be carried out according to two variants.

According to a first variant, the ionic liquid phase containing the organometallic system may be treated with the relevant metal with the oxidation state 0. The quantity of M$^0$ added is between 0.5 and 2 equivalents relative to the compound RX initially added, preferably in the region of 1 equivalent. The regeneration of the active species of the metal Mb may be carried out at a temperature of between 20° C. and 90° C., preferably between 20° C. and 60° C., over a period of between 0.5 and 3 hours. The ionic liquid phase may then be thus reused for another ATRA reaction by simply adding the compound RX, the nitroxide and the organic solvent and by proceeding as described above. The reaction/regeneration of the organometallic system cycles may be performed several times.

According to a second variant, the regeneration of the organometallic system consists in simultaneously adding to the ionic liquid phase the compound RX, the nitroxide, the organic solvent and the metal with the oxidation state 0 in suitable proportions. The regeneration is thus carried out in situ and the (ATRA) reaction may occur as described above. This procedure can also be repeated several times.

Thus, one of the advantages of the present invention is that the organometallic system may be regenerated over several cycles without addition of metal salt and of ligand. This makes it possible to reduce the cost of the process by increasing the alkoxyamine productivity relative to the quantities of metal salt and of ligand which are used in a homogeneous system.

In addition, the process according to the invention has the advantage of being carried out with commercially available ligands. The reaction between the nitroxide (II) and the halocarbon compound ZX is fast.

The process according to the invention makes it possible to obtain alkoxyamines which are virtually free of metal M. The alkoxyamines obtained according to the process of the invention exhibit a content of metal M of less than 10 ppm.

The alkoxyamines are thus obtained with high yields by a process which is easy to carry out and which does not require expensive purification operations.

The process according to the invention applies most particularly to the preparation of alkoxyamines of formula:

(I)

from nitroxides of formula:

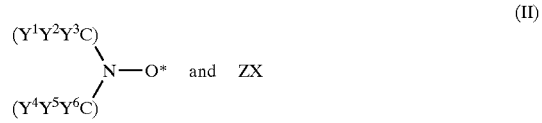
(II)

in which formulae the groups $Y^1$ to $Y^6$, which may be identical or different, represent a hydrogen atom, a linear or branched alkyl radical containing a number of carbon atoms ranging from 1 to 10, a cycloalkyl radical containing a number of carbon atoms ranging from 3 to 20, a halogen atom, a cyano radical, a phenyl radical, a hydroxyalkyl radical containing a number of carbon atoms ranging from 1 to 4, a dialkoxyphosphonyl or diphenoxyphosphonyl radical, an alkoxycarbonyl or alkoxycarbonylalkyl radical, or alternatively 2 or more of the groups $Y^1$ to $Y^6$ can be linked with the carbon atom which bears them to form cyclic structures, which can comprise one or more exocyclic functions chosen from: HO—, CH$_3$C(O)—, alkyl-C(O)O— or the linear or branched alkyl radical containing a number of carbon atoms ranging from 1 to 30, CH$_3$O—, H$_2$N—CH$_3$C (O)NH—, (CH$_3$)$_2$N—; or alternatively can comprise 1 or more exocyclic or endocyclic hetero atoms such as 0 or N;

Z is a residue of formula

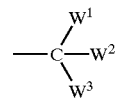

in which $W^1$, $W^2$ and $W^3$, which may be identical or different, represent a hydrogen atom, a linear or branched alkyl radical containing a number of carbon atoms ranging from 1 to 10, a phenyl radical, a benzyl radical, a cyano radical, a cycloalkyl radical containing a number of carbonatoms ranging from 3 to 12; a radical —(CH$_2$)rC(O) OW$^4$ in which W$^4$ represents a linear or branched alkyl containing a number of carbon atoms ranging from 1 to 6, r=0 to 6;

X represents a chlorine, bromine or iodine atom.

By way of illustration of nitroxides (II) which can be used according to the present invention, mention will be made of:
2,2,5,5-tetramethyl-1-pyrrolidinyloxy (generally sold under the trade name PROXYL);
3-carboxy-2,2,5,5-tetramethylpyrrolidinyloxy (commonly known as 3-carboxy PROXYL);
2,2,6,6-tetramethyl-1-piperidyloxy commonly known as TEMPO);
4-hydroxy-2,2,6,6-tetramethyl-1-piperidyloxy (commonly known as 4-hydroxy-TEMPO);
4-methoxy-2,2,6,6-tetramethyl-1-piperidyloxy (commonly known as 4-methoxy-TEMPO);

4-oxo-2,2,6,6-tetramethyl-1-piperidyloxy (commonly known as 4-oxo-TEMPO);

4-amino-2,2,6,6-tetramethyl-1-piperidyloxy (commonly known as 4-amino-TEMPO);

4-acetamido-2,2,6,6-tetramethyl-1-piperidyloxy (commonly known as 4-acetamido-TEMPO);

4-stearyloxy-2,2,6,6-tetramethyl-1-piperidyloxy (commonly known as 4-stearyloxy-TEMPO);

N-tert-butyl-1-phenyl-2-methylpropyl nitroxide,

N-(2-hydroxymethylpropyl)-1-phenyl-2-methylpropyl nitroxide,

N-tert-butyl-1-diethylphosphono-2,2-dimethylpropyl nitroxide,

N-tert-butyl-1-dibenzylphosphono-2,2-dimethylpropyl nitroxide,

N-tert-butyl-1-di(2,2,2-trifluoroethyl)-phosphono-2,2-dimethylpropyl nitroxide,

N-tert-butyl-[(1-diethylphosphono)-2-methylpropyl] nitroxide,

N-(1-methylethyl)-1-cyclohexyl-1-(diethylphosphono) nitroxide,

N-1-phenylbenzyl)-[(1-diethylphosphono)-1-methylethyl]nitroxide,

N-phenyl-1-diethylphosphono-2,2-dimethylpropyl nitroxide,

N-phenyl-1-diethylphosphono-1-methylethyl nitroxide,

N-(1-phenyl-2-methylpropyl)-1-diethylphosphono-methylethyl nitroxide, bis-1-oxyl-2,2,6,6-tetramethylpiperid-4-yl sebacate sold under the brand name "CXA 5415" by the company CIBA SPEC. CHEM.

By way of illustration of compounds ZX which can be used, mention will be made of the compounds of formula: $C_6H_5CH(CH_3)Br$, $C_6H_5CH_2Br$, $(CH_3)_2C(CN)Br$, $CH_3OC(O)C(CH_3)_2Br$, $CH_3OC(O)CH(CH3)Br$, $C_6F_{13}I$.

The alkoxyamines of formula (I) obtained according to the process of the present invention can be used for the polymerization and copolymerization of any monomer containing a carbon-carbon double bond which can undergo radical-mediated polymerization. The polymerization or copolymerization is carried out under the usual conditions known to those skilled in the art, taking into account the monomer(s) under consideration. The monomers under consideration may be a vinylaromatic monomer (styrene, substituted styrenes), a diene or an acrylic or methyacrylic monomer. The monomer may also be vinyl chloride, vinylidene difluoride or acrylonitrile.

The examples which follow illustrate the invention.

EXAMPLES

General Comments

The tests were carried out under an atmosphere of inert gas (argon or nitrogen) using Schlenk techniques (standard).

The 1-bromoethylbenzene and N-tert-butyl-1-diethylphosphono-2,2-dimethylpropyl nitroxide (DEPN) are degassed beforehand.

The solvent used is toluene, which is distilled beforehand under argon over sodium-benzophenone.

The ligands used are:

N,N,N',N',N''-pentamethyldiethyldiethylenetriamine, denoted hereinbelow as PMDETA, bipyridine, denoted hereinbelow as BIPY.

The alkoxyamines obtained were characterized by $^1H$, $^{13}C$ and $^{31}P$ NMR and by elemental analysis.

The residual copper contents were determined by the plasma atomic emission spectroscopy technique with detection by mass spectrometry, referred to. hereinbelow as ICP-MS (Inductively Coupled Plasma-Mass Spectrometry).

Preparation of the Ionic Liquids Used

1/Synthesis of 1-propyl-3-methylimidazolium Bromide 450 g of 1-bromopropane (3.66 mol) are loaded into a 1 l glass reactor. The mixture is heated to 70° C. and then 200 g of 1-methylimidazole (2.44 mol) are poured in dropwise, with stirring. The mixture is left to react for 1 h at 70° C. After returning to room temperature, the mixture is separated by decantation. The bottom ionic liquid phase is recovered, washed with toluene (1×100 ml), and then evaporated under vacuum. 475 g of 1-methyl-3-propylimidazolium bromide are obtained in the form of a yellow liquid. The product is used as a base without further purification.

2/Synthesis of 1-butyl-3-methylimidazolium Chloride 251.4 g of 1-chlorobutane (2.7 mol) are loaded into a 1 l glass reactor. The mixture is heated to 60° C., and then 148.6 g of 1-methylimidazole (1.8 mol) are poured in dropwise, with stirring. The mixture is left to react for 24 h at 80° C. The reaction mixture is evaporated under vacuum. 309 g of 1-butyl-3-methylimidazolium chloride are obtained in the form of a yellowish solid (yield=98%). The product is used as it is without further purification.

Example 1

Not in Accordance with the Invention

Preparation of N-tert-butyl-N-1-diethylphosphono-2,2-dimethylpropyl-O-1-phenylethylhydroxylamine

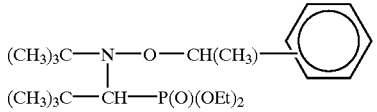

0.57 g of CuBr (4 mmol) and 1.25 g of BIPY (8 mmol) (BIPY/CuBr molar ratio =2) are introduced into a 100 ml Schlenk tube purged with argon. 0.74 g of (1-bromoethyl) benzene (4 mmol) and 0.68 g of 86% DEPN (2 mmol) dissolved in 9 ml of anhydrous toluene are added. The mixture is left to react for 48 hours at room temperature, with stirring. The reaction mixture is filtered through Celite. The filtrate is washed with aqueous 5% copper sulphate solution and then with water. The organic phase is dried over magnesium sulphate and the solvent is then evaporated off. A greenish oil containing copper is obtained, which is purified by chromatography on a column of silica using a 6/4 pentane/ether eluent. 0.75 g of N-tert-butyl-N-1-diethylphosphono-2,2-dimethylpropyl-0-1-phenylethyl-hydroxylamine is obtained (yield=95%) in the form of two diastereoisomers in 64/36 proportions determined from the $^{31}P$ spectrum of the crude mixture by integration of the signals at 23.14 and 24.36 ppm (I/II=64/36).

The analytical results are given below:

Isomer I:

$^{31}P$ NMR (CDCl$_3$): δ 23.14

$^1H$ NMR (CDCl$_3$): δ 0.88 (t, J$_{H-H}$=7.2 Hz, 3H): 1.27 (m, 21H); 1.55 (d, J$_{H-H}$=6.6 Hz, 3H) (s, 9H); 3.40 (d, J$_{H-P}$=26 Hz, 1H); 3.18–3.40 and 3.70–4.05 (m, 4H); 5.22 (q, J$_{H-H}$=6.6 Hz, 1H); 7.24–7.47 (m, 5H).

$^{13}C$ NMR (CDCl$_3$): δ 16.23 (2d, J$_{C-P}$=7 Hz, CH$_3$CH$_2$), 21.18 (s, CH$_3$CH), 28.19 (s, CH$_3$—C—CH), 30.63 (d, J$_{C-P}$=7 Hz, CH$_3$—CN), 35.33 (d, J$_{C-P}$=6 Hz, C—CH—P), 58.58 (d, J$_{C-P}$=7.5 Hz, C—CH$_3$), 61.4 (d, J$_{C-P}$=7 Hz,

CH$_2$—O), 70.06 (d, J$_{C-P}$=138.5 Hz, CH—P), 78.36 (s, CH—O), 127.33 (s, CH Ar), 127.81 (s, CH Ar), 127.88 (s, CH Ar), 143.31 (s, C Ar).

Microanalysis (C$_{21}$H$_{37}$NO$_4$P): % calculated C 63.12; H 9.59; N 3.51. % found C 63.01; H 9.60; N 3.42.

Isomer II:

$^{31}$P NMR (CDCl$_3$): δ 24.36

$^1$H NMR (CDCl$_3$): δ 0.82 (s, 9H); 1.22 (s, 9H), 1.29 (t, J$_{H-H}$=7.0 Hz, 3H); 1.32 (t, J$_{H-H}$=7.0 Hz, 3H); 1.58 (d, J$_{H-H}$=6.7 Hz, 3H); 3.32 (d, J$_{H-P}$=26.2 Hz, 1H); 3.9–4.2 and 4.3–4.4 (m, 4H); 4.97 (q, J$_{H-H}$=6.8 Hz, 1H); 7.17–7.3 (m, 5H);

$^{13}$C NMR (CDCl$_3$): δ 16.24 (d, J$_{C-P}$=7.1 Hz, CH$_3$CH$_2$), 16.71 (d, J$_{C-P}$=5.2 Hz, CH$_3$CH$_2$), 24.00 (s, CH$_3$CH), 28.50 (s, CH$_3$—C—CH), 30.12 (d, J$_{C-P}$=5.7 Hz, CH$_3$—C—N), 35.37 (d, J$_{C-P}$=5.8 Hz, C—CH—p), 58.80 (d, J$_{C-P}$=7.4 Hz, CH$_2$—O), 61.10 (s, C—N), 61:56 (d, J$_{C-P}$=6 Hz, CH$_2$—O), 69.84 (d, J$_{C-P}$=138.4 Hz, CH—P), 85.23 (s, CH—O), 126.96 (s, CH Ar), 127.08 (s, CH Ar), 127.95 (s, CH Ar), 145.36 (s, C Ar).

Microanalysis (C$_{21}$H$_{37}$NO$_4$P): % calculated C 63.12; H 9.59; N 3.51. % found C 63.05; H 9.51; N 3.50.

Example 2

In Accordance with the Invention
Preparation of N-tert-butyl-N-1-diethylphosphono-2,2-dimethylpropyl-O-1-phenylethylhydroxylamine in the Presence of 1-methyl-3-propylimidazolium Bromide 3.3 g of CuBr (23 mmol), 1.6 g of PMDETA (9 mmol), 1.46 g of Cu(0) (23 mmol) and 32 g of 1-methyl-3-propylimidazolium are loaded into a 250 ml reactor provided with stirring using a turbine rotating at 500 rpm, purged with argon. 4.3 g of (1-bromoethyl)benzene (23 mmol) and 5.56 g of 90% DEPN (17 mmol) dissolved in 60 g of degassed toluene are added. The mixture is left to react, with stirring, at room temperature. The disappearance of DEPN is monitored by TLC. After 24 hours, the reaction mixture is separated by decantation. The organic phase is recovered and the ionic liquid phase is extracted with 60 g of toluene. The combined organic phases are washed with water (2×60 g). The solvent is evaporated off to give 6.6 g of N-tert-butyl-N-1-diethylphosphono-2,2-dimethylpropyl-O-1-phenylethylhydroxylamine in the form of a colourless oil (yield=97%,-purity=97%).

The residual copper content is less than 10 ppm.

The ionic liquid phase extracted is recycled once by adding thereto 1.46 g of Cu° (23 mmol), 4.3 g of (1-bromoethyl)benzene (23 mmol), 5.56 g of 90% DEPN (17 mmol) dissolved in 60 g of degassed toluene and the procedure is carried out at described above. The ionic liquid phase extracted from this first recycling is recycled by adding thereto, as above, the same reagents and solvent in identical quantities. A total of 4 recyclings are carried out. The results are summarized in the following Table 1.

TABLE 1

| Test | Load | T (° C.) | t (h) | Yield (%) |
|---|---|---|---|---|
| 1 | a | 20 | 24 | 97 |
| recycling 1 | b | 20 | 24 | 95 |
| recycling 2 | b | 20 | 24 | 95 |
| recycling 3 | b | 20 | 24 | 97 |
| recycling 4 | b | 20 | 24 | 95 |

Load a: CuBr=3.3 g; PMDETA=1.6 g; Cu°=1.46 g; (1-bromoethyl)benzene=4.3 g; DEPN 90%=5,6 g; toluene=60 g; 1-methyl-3-propylimidazolium=32 g Load b: Cu°=1.46 g; (1-bromoethyl)benzene=4.3 g; DEPN 90%=5.6 g; toluene=60 g Overall, we produced 32.4 g of N-tert-butyl-N-1-diethylphosphono-2,2-dimethylpropyl-O-1-phenylethylhydroxylamine (81 mmol) per 3.3 g of CuBr (23 mmol), 1.6 g of PMDETA (9 mmol) and 7.3 g of Cu° (115 mmol).

Preparation of N-tert-butyl-N-1-diethylphosphono-2,2-dimethylpropyl-O-1-phenylethylhydroxylamine in the Presence of 1-propyl-3-methylimidazolium Bromide In this example, the regeneration of the active species is carried out prior to the reaction.

3.3 g of CuBr (23 mmol), 4.0 g of PMDETA (23 mmol), 1.46 g of Cu° (23 mmol) and 32 g of 1-methyl-3-propylimidazolium are loaded into a 250 ml reactor purged with argon. 4.3 g of (1-bromoethyl)benzene (23 mmol) and 6.4 g of 92% DEPN (20 mmol) dissolved in 40 g of degassed toluene are added. The mixture is left to react for 6 h, with stirring, at 20° C. The reaction mixture is separated by decantation. The organic phase is recovered and the ionic liquid phase is extracted with 20 g of toluene. The combined organic phases are washed with water (2×40 g). The solvent is evaporated off to give 7.6 g of N-tert-butyl-N-1-diethylphosphono-2,2-dimethylpropyl-O-1-phenylethylhydroxylamine in the form of a colourless oil (yield =95%).

1.46 g of Cu° and 20 g of toluene are then added to the ionic liquid phase extracted, and then the mixture is heated for 3 h at 60° C. Another reaction can then be carried out by adding 4.3 g of (1-bromoethyl)benzene (23 mmol), 6.4 g of 92% DEPN (20 mmol) dissolved in 20 g of toluene. According to this procedure, 4 recyclings were carried out with reaction times as indicated in Table 2. The results are summarized in the following Table 2:

TABLE 2

| Test | Load | T (° C.) | t (h) | Yield (%) |
|---|---|---|---|---|
| 1 | a | 20 | 6 | 95 |
| recycling 1 | b | 20 | 7 | 94 |
| recycling 2 | b | 20 | 7 | 96 |
| recycling 3 | b | 20 | 7 | 94 |
| recycling 4 | b | 20 | 12 | 95 |

Load a: CuBr=3.3 g; PMDETA=4.0 g; Cu°=1.46 g; (1-bromoethyl)benzene=4.3 g; DEPN 92%=6.4 g; toluene= 40 g; 1-methyl-3-propylimidazolium=32 g Load b: Cu°=1.46 g; toluene=20 g (regeneration 3 h at 60° C.); and then (1-bromoethyl)benzene=4.3 g; DEPN 92%= 6.4 g; toluene=20 g Overall, we produced 37.9 g of N-tert-butyl-N-1-diethylphosphono-2,2-dimethylpropyl-O-1-phenylethylhydroxylamine (95 mmol) per 3.3 g of CuBr (23 mmol), 4 g of PMDETA (23 mmol) and 7.3 g of Cu° (115 mmol).

Example 4

Preparation of N-tert-butyl-N-1-diethylphosphono-2,2-dimethylpropyl-O-1-phenylethylhydroxylamine in the Presence of 1-butyl-3-methylimidazolium Chloride 3.3 g of CuBr (23 mmol), 4.0 g of PMDETA (23 mmol), 1.46 g of Cu(0) (23 mmol) and 32 g of 1-butyl-3-methylimidazolium and 5 g of water are loaded into a 250 ml reactor purged with argon. 4.3 g of (1-bromoethyl)benzene (23 mmol) and 5.4 g of 92% DEPN (17 mmol)

dissolved in 40 g of degassed toluene are added. The mixture is left to react for 3 h, with stirring, at 35° C. The reaction mixture is separated by decantation. The organic phase is recovered and the ionic liquid phase is extracted with 20 g of toluene. The combined organic phases are washed with water (2×40 g). The solvent is evaporated off to give 6.45 g of N-tert-butyl-N-1-diethylphosphono-2,2-dimethylpropyl-O-1-phenylethylhydroxylamine in the form of a colourless oil (yield=95%).

The regeneration of the active species is carried prior to the reaction according to the conditions hereinbelow.

1.46 g of Cu° and 20 g of toluene are then added to the ionic liquid phase extracted, and then the mixture is heated for 2 h at 35° C.: Another reaction can then be carried out by adding 4.3 g of (1-bromoethyl)benzene (23 mmol), 5.4 g of 92% DEPN (17 mmol) dissolved in 20 g of toluene. According to this procedure, 9 recyclings were carried out with reaction times as indicated in Table 3. The results are summarized in the following Table 3:

TABLE 3

| Test | Load | T (° C.) | t (h) | Yield (%) |
|---|---|---|---|---|
| 1 | a | 35 | 3 | 95 |
| recycling 1 | b | 35 | 3 | 94 |
| recycling 2 | b | 35 | 3 | 97 |
| recycling 3 | b | 35 | 3 | 95 |
| recycling 4 | b | 35 | 3 | 93 |
| recycling 5 | b | 35 | 1.5 | 92 |
| recycling 6 | b | 35 | 3 | 96 |
| recycling 7 | b | 35 | 3 | 97 |
| recycling 8 | b | 35 | 3 | 95 |
| recycling 9 | b | 35 | 3 | 95 |

Load a: CuBr=3.3 g; PMDETA=4.0 g; Cu°=1.46 g; (1-bromoethyl)benzene=4.3 g; DEPN 92%=5.4 g; toluene=40 g; 1-butyl-3-methylimidazolium=32 g; $H_2O$=5 g Load b: Cu°=1.46 g; toluene=20 g (regeneration 2 h at 35° C.); and then (1-bromoethyl)benzene=4.3 g; DEPN 92%=5.4 g; toluene=20 g Overall, we produced 64.5 g of N-tert-butyl-N-1-diethylphosphono-2,2-dimethylpropyl-O-1-phenylethylhydroxylamine (0.161 mol) per 3.3 g of CuBr (0.023 mol), 4 g of PMDETA (0.023 mol) and 14.6 g of Cu° (0.230 mol).

What is claimed is:

1. In a process for preparing alkoxyamines of formula:

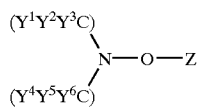

(I)

from nitroxides of formula:

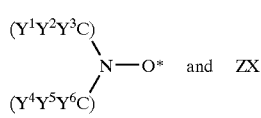

(II)

in which formulae the groups $Y^1$ to $Y^{6,}$ which may be identical or different, represent a hydrogen atom, a linear or branched alkyl radical containing a number of carbon atoms ranging from 1 to 10 inclusive, a cycloalkyl radical containing a number of carbon atoms ranging from 3 to 20, a halogen atom, a cyano radical, a phenyl radical, a hydroxyalkyl radical containing a number of carbon atoms ranging from 1 to 4 inclusive, a dialkoxyphosphonyl or diphenoxyphosphonyl radical, an alkoxycarbonyl or alkoxycarbonylalkyl radical, or alternatively 2 or more of the groups $Y^1$ to $Y^6$ can be linked with the carbon atom which bears them to form cyclic structures, which optionally comprise one or more exocyclic functions chosen from: HO—., $CH_3C(O)$—, alkyl-C(O)O— or a linear or branched alkyl radical containing a number of carbon atoms ranging from 1 to 30 inclusive, $CH_3O$—, $H_2N$—$CH_3C(O)(NH$—, $(CH_3)_2N$—; or alternatively can comprise 1 or more exocyclic or endocyclic hetero atoms chosen from O or N;

Z is a residue of formula

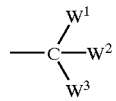

in which $W^{1,}$ $W^2$ and $W^{3,}$ which may be identical or different, represent a hydrogen atom, a linear or branched alkyl radical containing a number of carbon atoms ranging from 1 to 10 inclusive, a phenyl radical, a benzyl radical, a cyano radical, a cycloalkyl radical containing a number of carbon atoms ranging from 3 to 12 inclusive; a radical —$(CH_2)_rC(O)OW^4$ in which $W^4$ represents a linear or branched alkyl containing a number of carbon atoms ranging from 1 to 6 inclusive, r=0 to 6;

X represents a chlorine, bromine or iodine atom, said process comprising reacting said nitroxide (II) with a halocarbon compound ZX, in the presence of an organometallic system $MA_n(L)_y$ (III) in which:

M comprises $M^n$, a transition metal with an oxidation state n such that it can participate in a redox reaction with a transferable atom or group, A represents a halogen atom, a carboxylate group or a triflate group, L represents a ligand for the metal M, y is equal to 1, 2 or 3, n is equal to 1, or 2, according to the scheme:

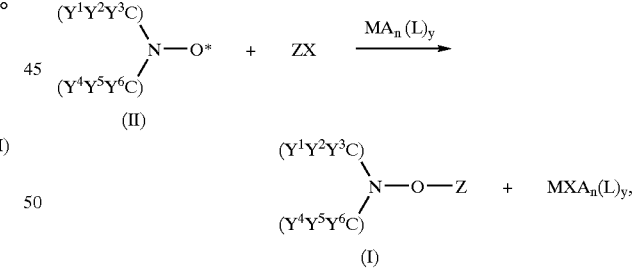

the improvement comprising conducting said process in a biphasic medium comprising at least one ionic liquid and an organic solvent which is immiscible with said ionic liquid.

2. A process according to claim 1, comprising carrying out the following steps:

a) a metal salt $M^nA_n$ and optionally a metal M with an oxidation state of zero, a ligand L, at least one ionic liquid, an organic solvent, the halo carbon compound ZX and the nitroxide (II) are mixed, with stirring, in a ZX/nitroxide (II) molar ratio ranging from 1 to 1.5 inclusive;

b) the reaction medium is kept stirring at a temperature of between 20° C. and 90° C., until the nitroxide (II) has completely disappeared; and then c) the stirring is stopped, the mixture is separated by decantation, the organic phase is recovered and optionally washed with water, and then d) the alkoxyamine (I) is isolated from the organic phase by evaporating the organic solvent under reduced pressure, and e) optionally, the ionic liquid phase is recycled at least once, with regeneration of the active species of the metal M designated as M''.

3. A process according to claim 1 wherein the ionic liquid comprises a N,N'-dialkylimidazolium salt.

4. A process according to claim 3, wherein the ionic liquid comprises at least one of 1-butyl-3-methylimidazolium chloride, 1-propyl-3-methylimidazolium chloride and 1-propyl-3-methylimidazolium bromide.

5. A process according to claim 1, wherein the ligand L for the metal M in the organometallic system (III) is chosen from the compounds represented by the general formula (IV):

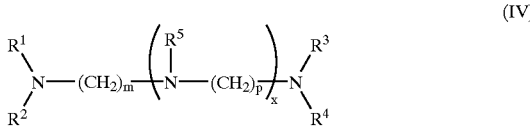

(IV)

in which $R^1$, $R^2$, $R^3$ and $R^4$, which may be identical or different, represent a hydrogen atom, a linear or branched alkyl group containing a number of carbon atoms ranging from 1 to 10 inclusive, $R^5$ represents a hydrogen atom, a linear or branched alkyl group containing a number of carbon atoms ranging from 1 to 10 inclusive, a residue

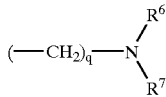

in which $R^6$ and $R^7$ have the same meanings as $R^5$, or alternatively at least two of the radicals $R^1$, $R^2$, $R^3$, $R^4$ and $R^5$ may be linked together to form a ring; m, p and q, which may be identical or different, represent integers ranging from 1 to 4 inclusive, x ranging from 0 to 4 inclusive.

6. A process according to claim 1, wherein M represents Cu(I), Fe(II) or Ni(II).

7. A process according to claim 1 wherein A represents a bromine atom and X represents a chlorine atom or a bromine atom.

8. A process according to claim 1 wherein the ZX/nitroxide (II) molar ratio is about 1.

9. A process according to claim 1, wherein the metal salt $MA_n$ is a metal halide of the formula $M^nX_n$ in which the superscript n of the metal M represents the oxidation state of said metal and is equal to 1 or 2.

10. A process according to claim 9, wherein the metal halide $M^nX_n$ is CuBr.

11. A process according to claim 1, wherein the molar ratio L/active species M'' ranges from 0.2 to 4 inclusive.

12. A process according to claim 8, characterized in that the molar ratio L/M'' ranges from 0.4 to 2 inclusive.

13. A process according to claim 1, wherein the organic solvent is an aromatic hydrocarbon.

14. A process according to claim 13, wherein the aromatic hydrocarbon is toluene.

15. A process according to claim 1, wherein the ligand L is N,N,N',N',N''-pentamethyldiethylenetriamine (PMDETA) or N,N-dimethyldipropylenetriamine (DMAPAPA).

16. A process according to claim 2, wherein Step (b) is conducted at 20° to 35°C.

17. A process according to claim 2, comprising conducting step (e) 1–11-times.

18. A process according to claim 5, wherein the linear or branched alkyl group contain 1–4 carbon atoms and m, p, and q represents 2.

19. A process according to claim 6, wherein M represents Cu(I).

20. A process according to claim 15, wherein M represents Cu(I).

21. A process according to claim 20, wherein the organic solvent is an aromatic hydrocarbon.

* * * * *